DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED AUGUST 6, 1974

925 O.G. 8

T925,003

ECG MONITORING METHOD

Raymond E. Bonner, Yorktown Heights, N.Y., assignor to International Business Machines Corporation, Armonk, N.Y.

Continuation of application Ser. No. 51,236, July 30, 1970. This application June 29, 1973, Ser. No. 375,284

Int. Cl. A61b *5/04*

U.S. Cl. 444—1

6 Sheets Drawing. 32 Pages Specification

Figure 1:
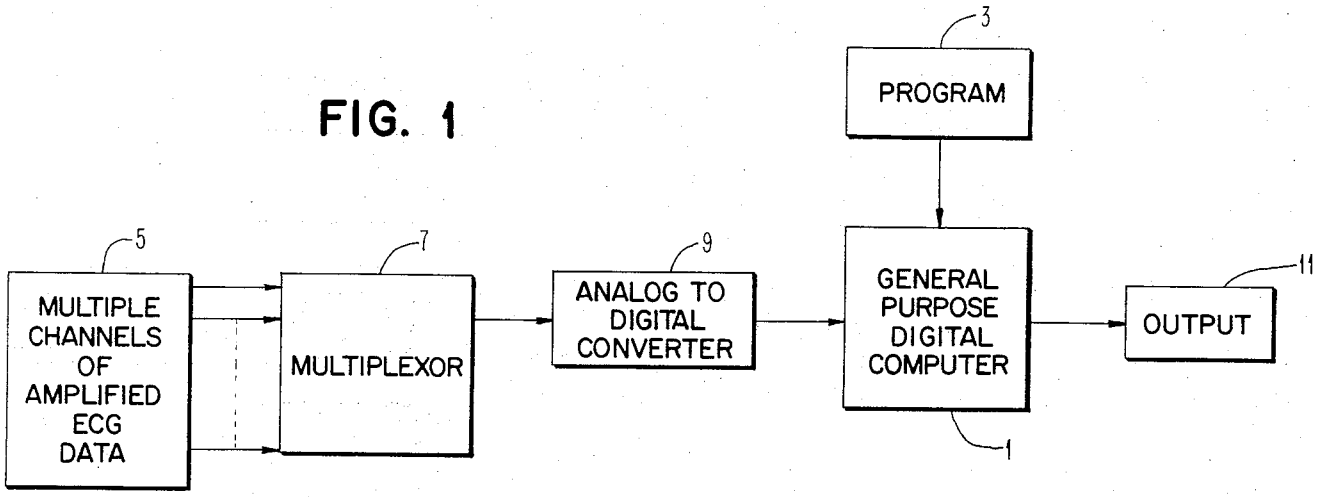
Figure 2:
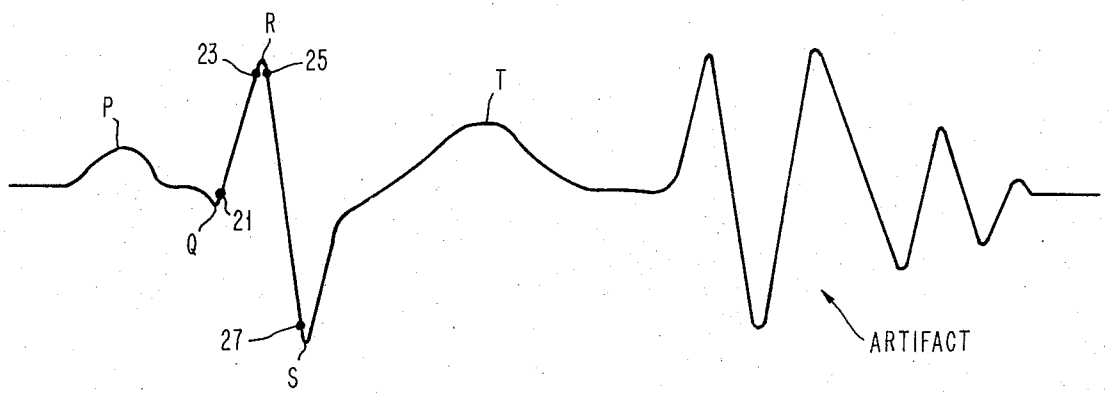
Figure 3:
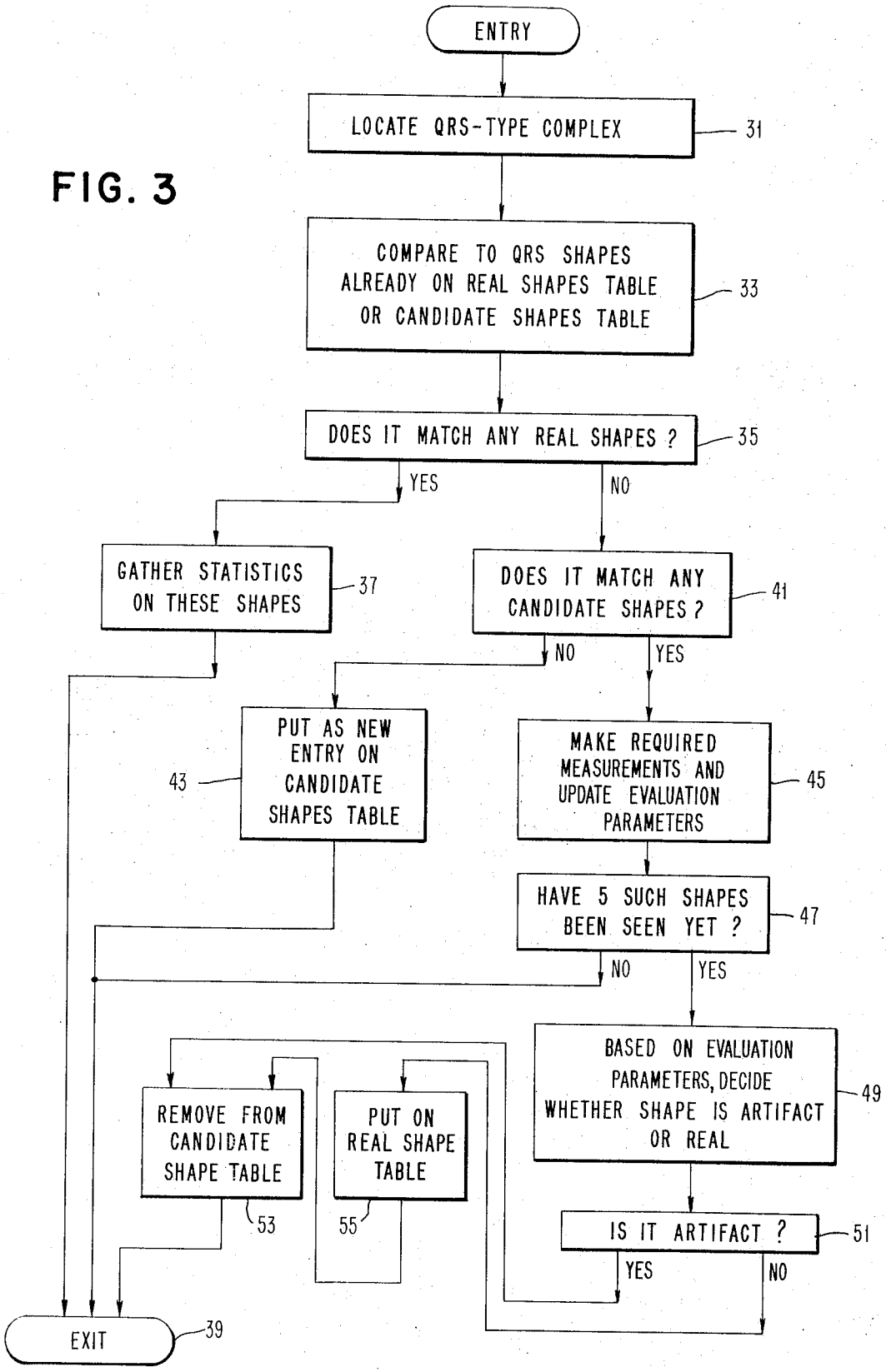
Figure 4:
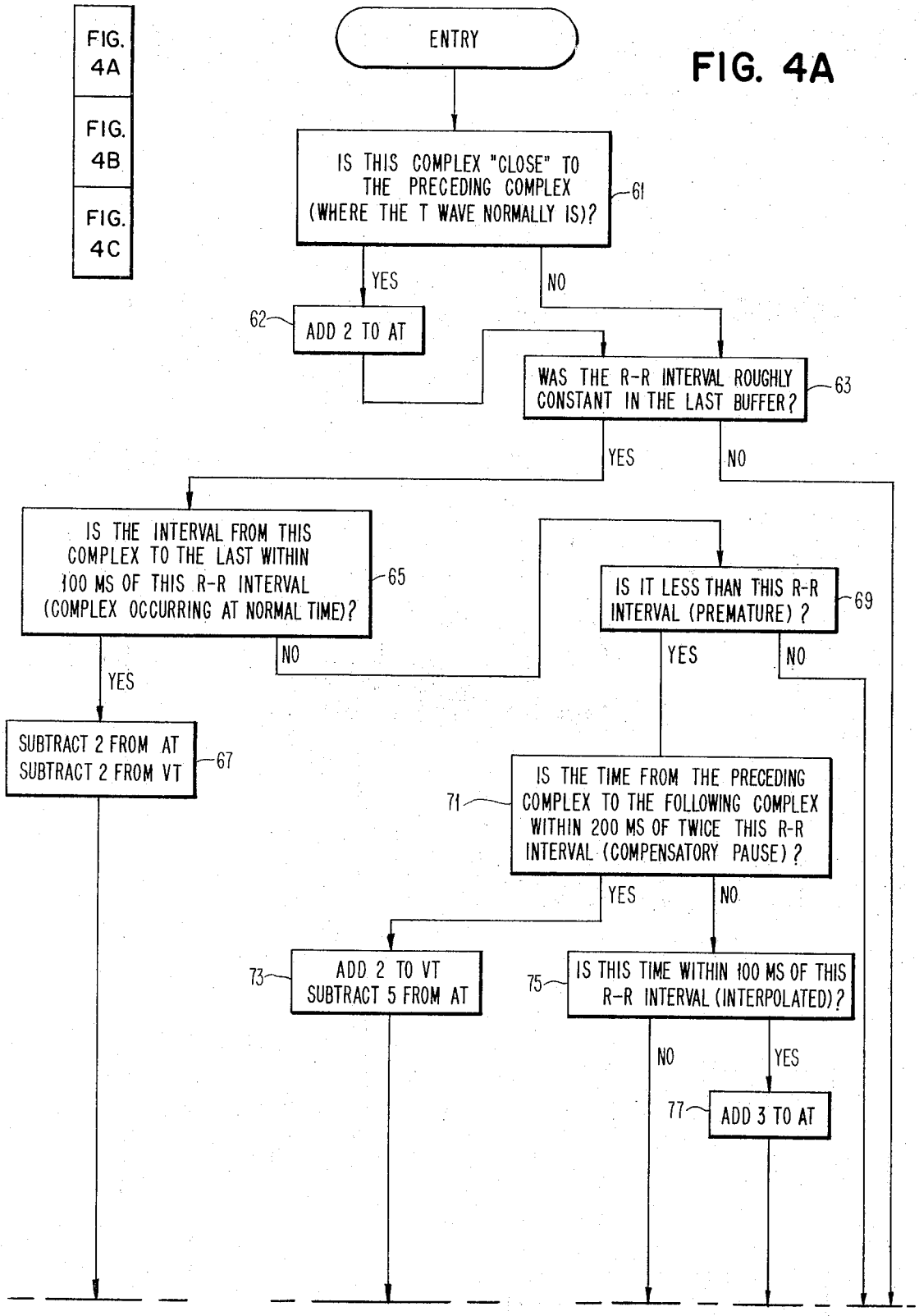
Figure 4B:
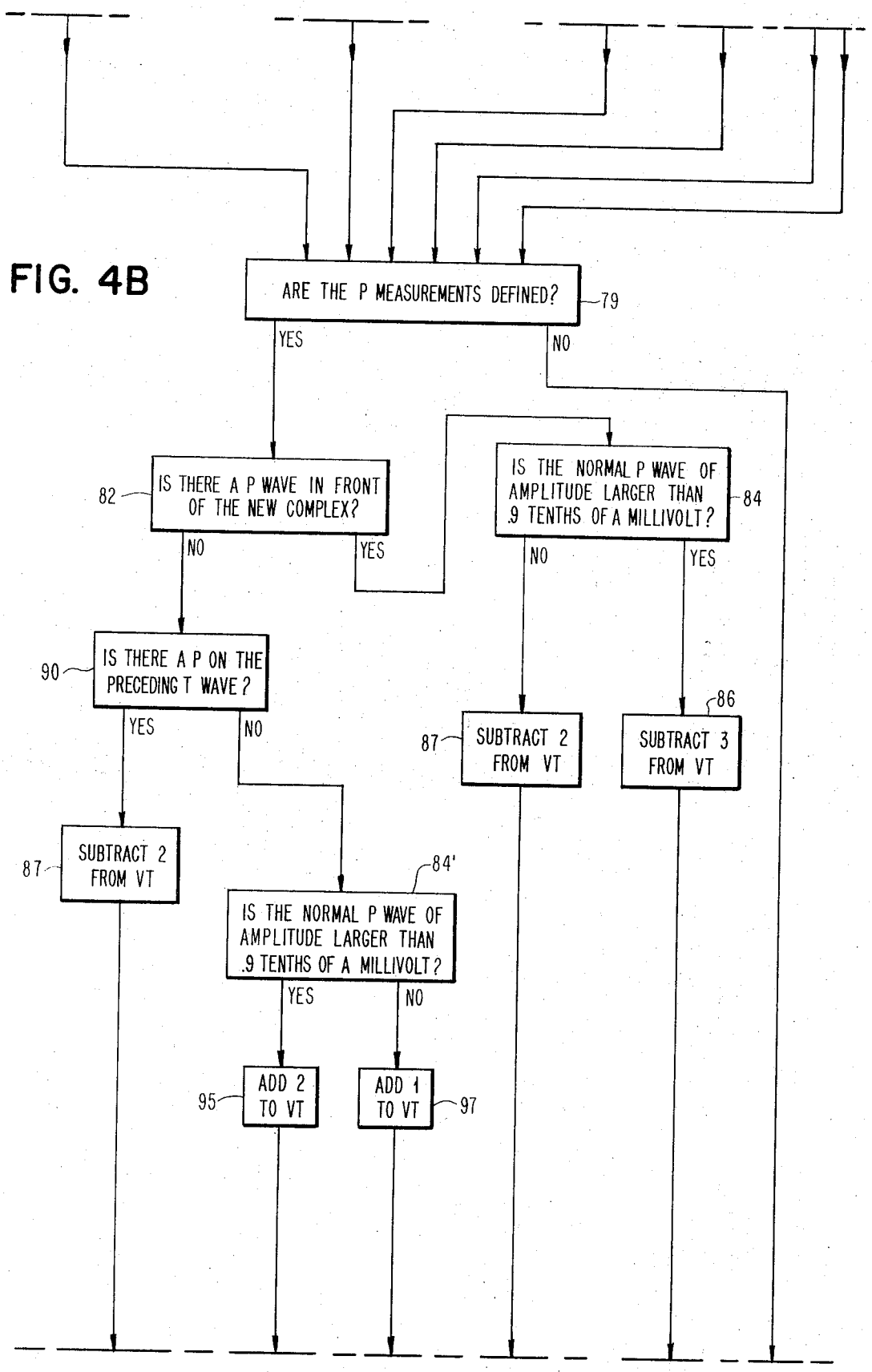
Figure 4C:
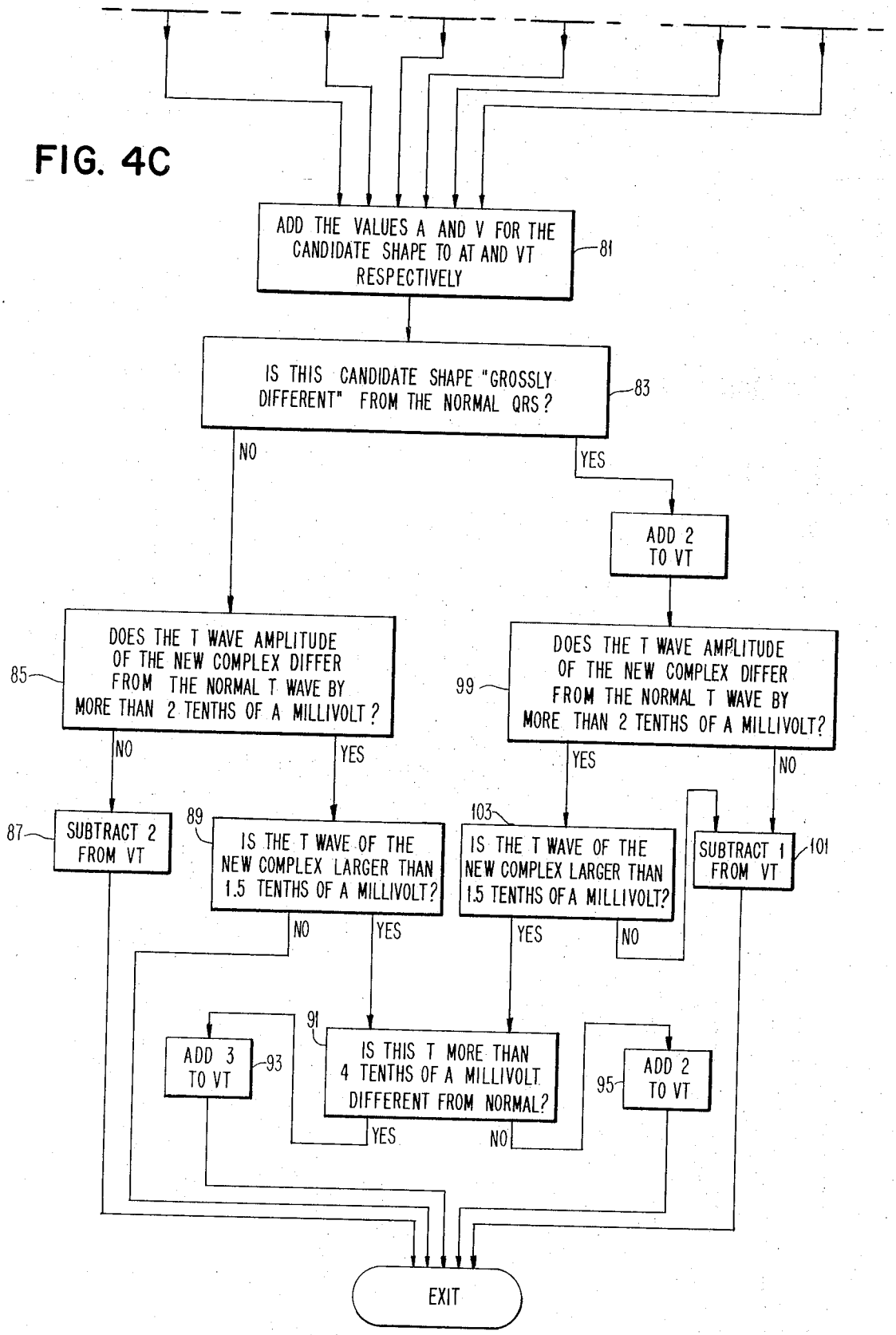
Figure 5:
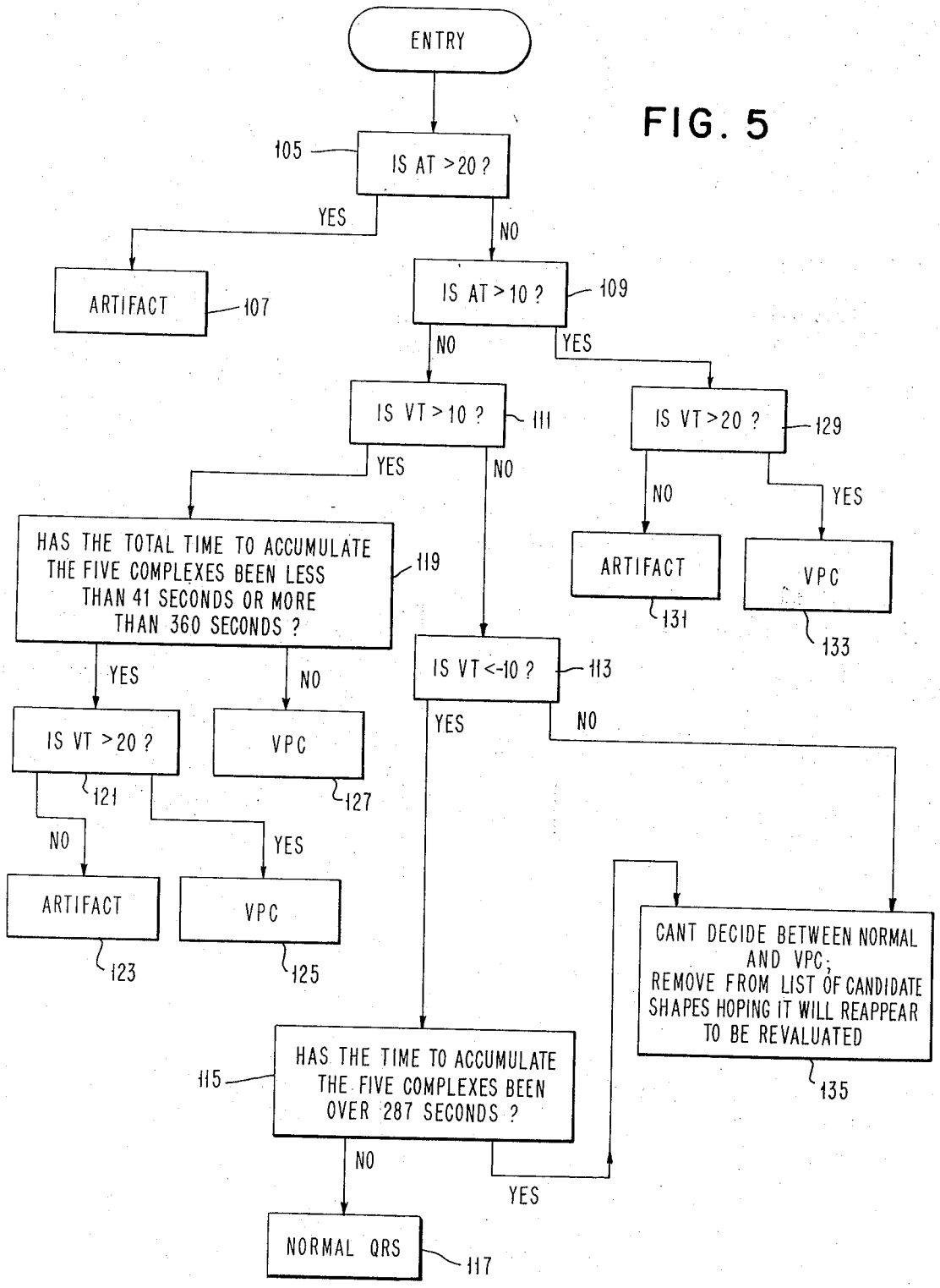

Methods of monitoring and analyzing electrocardiographic signal data, to identify arrhythmias and the like, require selection of real QRS complexes and rejection of artifacts that look like real QRS complexes. To achieve this end, two tables of QRS complex shapes are employed in a digital computer, with the first table containing the shapes of different versions of real QRS complexes and the second table containing the shapes of QRS-type complexes which have not yet been determined real but are candidates for being considered real. As shown in FIG. 3, a located QRS-type complex is first compared to the various shapes on the "real shapes" table, as represented by the steps of blocks 33 and 35. If it compares with none, it is then compared to the shapes on the "candidate shapes" table, as represented by the steps of blocks 33–41. If it compares with none of the shapes on the "candidate shapes" table, it is added thereto as a new candidate, as shown at step 43. If it compares with one of the shapes on the "candidate shapes" table, that fact is noted at step 45 and more credence is given that shape as being a possible new version of a real QRS complex. Measurements are also made at step 45 for evaluating candidate shapes and decision logic is employed at step 49 to ultimately decide whether or not a candidate shape, after having been seen several times, is a new version of a real QRS complex.

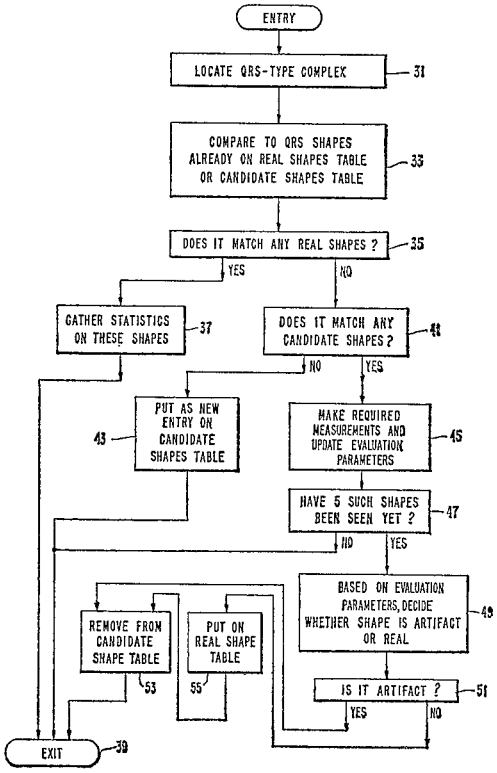

EGG MONITORING METHOD

Original Filed July 30, 1970 6 Sheets-Sheet 1

INVENTOR
RAYMOND E. BONNER

BY John A. Gordan
ATTORNEY